United States Patent
Dendorfer

(10) Patent No.: US 11,685,887 B2
(45) Date of Patent: Jun. 27, 2023

(54) SYSTEM AND METHOD FOR DETERMINING A FORCE APPLIED TO OR GENERATED BY A CELL OR TISSUE CULTURE

(71) Applicant: Andreas Dendorfer, Grafelfing (DE)

(72) Inventor: Andreas Dendorfer, Grafelfing (DE)

(73) Assignee: Andreas Dendorfer, Grafelfing (DE)

( * ) Notice: Subject to any disclaimer, the term of this patent is extended or adjusted under 35 U.S.C. 154(b) by 1107 days.

(21) Appl. No.: 15/781,454

(22) PCT Filed: Dec. 2, 2016

(86) PCT No.: PCT/EP2016/079660
§ 371 (c)(1),
(2) Date: Jun. 4, 2018

(87) PCT Pub. No.: WO2017/093529
PCT Pub. Date: Jun. 8, 2017

(65) Prior Publication Data
US 2020/0255789 A1    Aug. 13, 2020

(30) Foreign Application Priority Data
Dec. 4, 2015    (EP) .................................... 15198044

(51) Int. Cl.
*C12M 1/42*        (2006.01)
*G01L 1/12*        (2006.01)

(52) U.S. Cl.
CPC ............ *C12M 35/04* (2013.01); *C12M 35/06* (2013.01); *G01L 1/127* (2013.01)

(58) Field of Classification Search
CPC ......... C12M 35/04; C12M 35/06; C12N 5/08; G01L 1/127
See application file for complete search history.

(56) References Cited

U.S. PATENT DOCUMENTS 5,686,303 A * 11/1997 Korman ................. C12M 21/08
435/325
6,673,597 B2 * 1/2004 Wolf ...................... C12M 35/02
435/298.2

(Continued)

FOREIGN PATENT DOCUMENTS

DE        DD257294      *  6/1988
WO     2003060059 A2    7/2003

(Continued)

OTHER PUBLICATIONS

Govoni, M; Muscari, C.; Guarnieri, C.; Giodano, E., "Mechanostimulation protocols for cardiac Tissue engineering", Biomed Res. Int., (2013).

(Continued)

*Primary Examiner* — William H. Beisner

(57) ABSTRACT

Technologies and implementations for a system and method for determining a force applied to a cell or tissue culture is disclosed. The system and method may include an elastic element mounted in or suitable for mounting in a culture chamber. The elastic element may be adapted to be coupled with the cell or the tissue culture such that a force applied to the cell or the tissue culture leads to a deflection of the elastic element against a restoring force. A magnetic field sensor may be mounted outside said culture chamber. The magnetic (Continued)

field sensor may be adapted to detect a change of magnetic field attributable to a corresponding movement of a magnetic element upon deflection.

24 Claims, 6 Drawing Sheets

(56) References Cited

U.S. PATENT DOCUMENTS

| | | | | |
|---|---|---|---|---|
| 9,005,958 | B2* | 4/2015 | Watanabe | C12M 25/02 435/284.1 |
| 2001/0043918 | A1* | 11/2001 | Masini | C12M 35/04 424/93.7 |
| 2003/0091979 | A1 | 5/2003 | Eschenhagen | |
| 2004/0255687 | A1* | 12/2004 | Dukart | G01L 1/14 73/779 |
| 2005/0249667 | A1* | 11/2005 | Tuszynski | A61B 8/08 424/9.3 |
| 2006/0105357 | A1 | 5/2006 | Benesch et al. | |
| 2012/0296577 | A1* | 11/2012 | Garshelis | G01L 1/125 702/42 |
| 2017/0260488 | A1* | 9/2017 | Costa | C12M 41/48 |

FOREIGN PATENT DOCUMENTS

| | | | | |
|---|---|---|---|---|
| WO | | 2010006608 A1 | 1/2010 | |
| WO | WO-2014210388 A1 * | | 12/2014 | ........ B01L 3/502746 |

OTHER PUBLICATIONS

Rangarajan, S; Madden, L.; Bursac, N., "Use of flow, electrical, and mechanical stimulation to promote engineering of striated muscles", Annals of Biomedical Engineering, (2014), vol. 42, No. 7, pp. 1391-1405.

Kensah, G. et al., "A novel miniaturized multimodal bioreactor for continuous in situ assessment of bioartificial cardiac tissue during stimulation and maturation", Tissue Engineering. Part C, Methods, (2011), vol. 17, No. 4, pp. 463-473.

Lu, L. et al., "Design and validation of a bioreactor for simulating the cardiac niche: a system incorporating cyclic stretch, electrical stimulation, and constant perfusion", Tissue Engineering. Part A, (2013), vol. 19, No. 3-4 pp. 403-414.

Mathur, A et al., "Human iPSC-based cardiac microphysiological system for drug screening applications" Scientific Reports, (2015), vol. 5, p. 8883.

Chopra A. et al, "Cardiac myocyte remodeling mediated by N-cadherin-dependent mechanosensing", Am J Physiol Heart Circ Physiol., (2011), vol. 300, No. 4, pp. H1252-H1266.

Chaturvedi R.R. et al, "Passive stiffness of myocardium from congenital heart disease and implications for diastole", Circulation, (2010), vol. 121, No. 8, pp. 979-988.

Kim Sa. et al., "Alterations of carotid arterial mechanics preceding the wall thickening in patients with hypertension" Atherosclerosis, (2016), vol. 248, pp. 84-90.

Brandenburger M. et al., "Organotypic slice culture from human adult ventricular myocardium", Cardiovasc Res, (2012), vol. 93, No. 1, pp. 50-59.

Hassaballah A.L. et al., "An inverse finite element method for determining the tissue compressibility of human left ventricular wall during the cardiac cycle", PLOS One, (2013), vol. 8, No. 12, page E82703.

Stoppel W.L. et al, "Electrical and mechanical stimulation of cardiac cells and tissue constructs", Adv Drug Deliver Rev, (2016), vol. 96, pp. 135-155.

PCT International Search Report and PCT Written Opinion of the International Searching Authority, PCT/EP2016/079660, dated Feb. 17, 2017.

* cited by examiner

SYSTEM AND METHOD FOR DETERMINING A FORCE APPLIED TO OR GENERATED BY A CELL OR TISSUE CULTURE

RELATED APPLICATION

This application claims the benefit of priority to Patent Cooperation Treaty Application PCT/EP2016/079660, filed on Dec. 2, 2016, titled A SYSTEM AND METHOD FOR DETERMINING A FORCE APPLIED TO OR GENERATED BY A CELL OR TISSUE CULTURE, which in turn, claims priority to European Patent Application EP15198044.8, filed on Dec. 4, 2015, titled A SYSTEM AND METHOD FOR DETERMINING A FORCE APPLIED TO OR GENERATED BY A CELL OR TISSUE CULTURE, both of which are incorporated herein by reference in their entirety.

FIELD OF THE INVENTION

The present invention is in the field of biomedical technology. In particular, the present invention relates to the measurement of a force applied to or generated by a cell or tissue culture arranged in a culture chamber of a bioreactor.

BACKGROUND OF THE INVENTION

Living cells are capable of sensing forces and strains, allowing them to adapt to their natural environment. When cultivating cells or tissue in a cell culture, it is therefore desirable to apply similar forces to the cells or tissue, such that the cultivated cells or tissue will acquire their natural functionality.

An important example of cell or tissue cultivation is the engineering of bioartificial cardiac tissue, which can be transplanted as an artificial patch to a patient, or which could be used in the examination of the effects of drugs on cardiac tissue. It has been found that by simulating natural mechanical stretch and strain, in combination with stimulated contraction, the cultivated cells or tissue can acquire the natural function and a similar behavior as in a living organism. For this purpose incubation chambers have been proposed for stimulating the natural cell mechanics, as for example described in Govoni, M., Muscari, C., Guarnieri, C., Giodano, E., 2013. *Mechanostimulation protocols for cardiac Tissue engineering. BioMed Res. Int.*, ID918640 and in Rangarajan, S., Madden, L. & Bursac, N., 2014, *Use of flow, electrical, and mechanical stimulation to promote engineering of striated muscles. Annals of Biomedical Engineering,* 42(7), pp. 1391-1405 and US 2006/105357 A1.

Properly stimulating the cell mechanics, however, requires an appropriate control of the forces applied to the cell or tissue culture, which in turn requires a measurement of the forces applied. In addition, in many instances it will be advantageous or even necessary to measure the force generated or produced by the tissue itself, such as cardiac tissue, upon electrical stimulation thereof. For measuring these forces, conventional force sensors, load cells or the like can in principle be used. However, the cultivation of the cells or tissue requires a humid, sterile and biocompatible environment, under which conventional force sensors or load cells are usually not operable. In particular, the electronics of such force sensors or load cells are usually incompatible with the humid or wet environment inside the culture chambers.

For this reason, in Kensah, G. et al., 2011, *A novel miniaturized multimodal bioreactor for continuous in situ assessment of bioartificial cardiac tissue during stimulation and maturation. Tissue Engineering. Part C, Methods,* 17(4), pp. 463-473, in Lu, L. et al., 2013. *Design and validation of a bioreactor for simulating the cardiac niche: a system incorporating cyclic stretch, electrical stimulation, and constant perfusion. Tissue Engineering. Part A,* 19(3-4), pp. 403-414 and in US 2003/091,979 A1, it has been proposed to arrange the force sensors outside the culture chamber, and to mechanically transfer the force to the outside of the culture chamber using levers or rods. However, this adds to the complexity of the system, is prone to generate measurement errors and makes it more difficult to ensure sterile environments inside the culture chamber.

In view of these difficulties, in some applications the direct measurement of the applied forces has been dispensed with completely, and has been replaced by an analysis of the deformation of the tissue, for example by optically monitoring the tissue and employing a suitable image analysis, as for example described in Mathur, A. et al., 2015, *Human iPSC-based cardiac microphysiological system for drug screening applications. Scientific Reports,* 5, p. 8883. However, this indirect assessment of the force is not truly equivalent to a direct measurement of the force, because the morphology of the tissue and hence its elasticity changes over time, so that any assumed relationship between the deformation of the tissue and the underlying force changes with time but can hardly be accounted for.

SUMMARY

An aspect of the present disclosure provides a system for determining a force applied to or generated by a cell or tissue culture arranged in a culture chamber, the system comprising an elastic element mounted in or suitable for mounting in said culture chamber, and a magnetic field sensor, which is separated from said elastic element by a separating wall or by a space for providing a separating wall in between. Said elastic element is adapted to be coupled with said cell or tissue culture such that a force applied to or generated by said cell or tissue culture leads to a deflection of said elastic element against a restoring force thereof, and said elastic element forms or comprises a magnetic element arranged such as to be moved upon deflection of said elastic element. Said magnetic field sensor is adapted to detect a change of magnetic field attributable to a corresponding movement of said magnetic element upon deflection of said elastic element.

According to the present disclosure, the elastic element is adapted to be coupled with the cell or tissue culture such that a force applied to or generated by said cell or tissue culture leads to a deflection of said elastic element against a restoring force thereof. Herein, the term "deflection" is understood to have a broad meaning and covers any deformation of the elastic element from a rest configuration, and includes for example an elongation as known from a spring and a bending known from a rod or beam. The elastic element comprises a magnetic element arranged such as to be moved upon deflection of said elastic element. It is also possible that the elastic element itself is a magnetic object, in which case the elastic element itself forms the magnetic element of the invention, which is likewise moved upon deflection of the elastic element. When in the following reference is made to the magnetic element, it shall be understood without further mention that this magnetic element could in some embodiments be the same as the elastic element.

The magnetic field sensor according to the present disclosure is separated from said elastic element by a separating wall, or by a space for providing a separating wall in between. Said magnetic field sensor is adapted to detect a change of magnetic field attributable to a corresponding movement of said magnet element upon deflection of said elastic element.

According to embodiments of the present disclosure, forces are hence measured with a two-part arrangement, comprising said elastic element and said magnetic field sensor, wherein the elastic element and the magnetic field sensor are devoid of direct mechanical coupling. This allows for separating the elastic element and the magnetic field sensor by a space sufficient for accommodating a separating wall in between. In particular, this construction allows for an arrangement where said elastic element is exposed to the environment inside said culture chamber and said magnetic field sensor is separated from the environment inside said culture chamber. The rationale behind this is that exposing the elastic element to the wet environment inside the culture chamber is of little concern, because elastic elements of various embodiments of the invention can easily withstand such conditions. Note in this regard that the cell or tissue culture will typically be immersed in a nutrition solution or the like, and that the elastic element will hence be exposed to either the vapor of such solution or to the solution itself. The magnetic field sensor, on the other hand, is an electric component which typically needs to be protected from the nutrition solution or from the humid atmosphere associated therewith. According to the construction of the present disclosure, this can be readily achieved because the magnetic field sensor is sufficiently separated from the elastic element such that a separating wall may be provided in between.

Herein, the "separating wall" can be any type of wall casing, encapsulation, coating or the like which is suitable for separating the magnetic field sensor from the atmosphere within the culture chamber. In some embodiments, however, said magnetic field sensor is mounted or suitable for mounting outside said culture chamber. In this case, the aforementioned "separating wall" may be formed by a wall of the culture chamber.

Note that the system of the present disclosure may or may not include the culture chamber itself. In other words, in some embodiments the system is formed by a culture chamber with the elastic element mounted on the inside and the magnetic field sensor mounted on the outside. However, in other embodiments, the system may only include the elastic element and the magnetic field sensor and could be combined with a culture chamber obtainable from different sources. Note further that in the present disclosure, the term "outside the culture chamber" shall have a broad meaning and shall cover any instance where the magnetic field sensor is separated from the environment to which the cell or tissue culture is exposed by a separator wall of the culture chamber.

As explained above, according to some embodiments of the invention, only the elastic element is exposed to the environment within the culture chamber, and hence, only the elastic element needs to be biocompatible, sterile and capable of withstanding the wet environment within the culture chamber, while the magnetic field sensor may be separated from this environment and hence does not need to meet these requirements. As the inventor has confirmed, even with the magnetic field sensor and the magnetic element on the elastic element being arranged on different sides of the separator wall of the culture chamber, the amount of deflection of the elastic element can be quantitatively assessed with high precision using the magnetic element and the magnetic field sensor, and in this way, the force applied to or generated by the cell or tissue culture can be assessed to high precision with very simple means. In particular, contrary to the prior art discussed above, a direct measurement of the force can be carried out without the need to transfer any mechanical forces from inside the culture chamber to the outside, and without the need to provide any electrical load cell or the like inside the culture chamber.

In some embodiments, said magnetic field sensor is suitable for measuring a magnetic field component in a direction perpendicular to the direction of motion of said magnetic element upon said deflection of said elastic element. As will be demonstrated with reference to a specific embodiment below, this allows for a magnetic field strength or magnetic flux density that is nearly proportional to the deflection over a certain range of deflections, which allows for a simple and precise assessment of the degree of deflection based on the measured magnetic field strength. In addition or alternatively, the magnetic field sensor may be suitable for measuring a magnetic field component in a direction parallel to the direction of motion of said magnetic element upon said deflection of said elastic element.

In some embodiments, said magnetic field sensor is suitable for measuring at least two, and in further embodiments at least three, linearly independent magnetic field components. By accounting for two or even three linearly independent magnetic field components, the actual deflection can be reconstructed from the measurement of the magnetic field sensor to even higher precision, and also over a larger range of deflections.

In some embodiments, the system further comprises a logic element suitable for translating a measurement result of said magnetic field sensor into a parameter representing the deflection of said elastic element and/or a force applied to or generated by said cell or tissue culture. In some of these embodiments, said measurement result to be translated by said logic element may represent at least two linearly independent magnetic field components. For example, the measurement result could be a set of magnetic field strength values corresponding to said at least two linearly independent magnetic field components. Alternatively, the measurement result could be a predetermined mathematical combination of such field strength values, as long as it depends on these two linearly independent magnetic field components.

Said logic element may comprise one or both of an integrated circuit, in particular an FPGA or an ASIC, and a micro processor.

In some embodiments, said elastic element comprises a rod or beam, and said deflection amounts to a bending of said rod or beam. In the present disclosure, the expression "comprises a rod or beam" shall also include the special case where the elastic element consists of said rod or beam. Employing a rod or beam as the elastic element for the purposes of some embodiments of the invention has a number of special technical advantages. One advantage is that due to its elongate shape, it allows for coupling with the cell or tissue culture close to the center of the culture chamber, but at the same time for arranging the magnetic element close to the wall of the culture chamber, thereby allowing the magnetic element to be arranged close to the magnetic field sensor disposed outside this culture chamber wall. A further advantage is that a rod or beam can be easily produced from inert, biocompatible materials, and that its manufacture is comparatively cheap, so that it can e.g. be provided as a disposable product at favorable costs.

In some embodiments, said rod or beam has a fixed end mounted or adapted for mounting on said culture chamber, and a free end opposite to said fixed end, wherein said magnetic element is arranged closer to the free end than to the fixed end, and, in some embodiments, is within less than 20%, and in further embodiments within less than 10%, of the length of said rod or beam from said free end. This way, even moderate deflections due to comparatively small forces applied to or generated by the cell or tissue culture will lead to a fairly large movement of the magnetic element, which can be measured with good relative precision.

In some embodiments, said rod or beam is made from stainless steel, and in particular from surgical stainless steel, and in some embodiments from austentic 316 stainless steel, martensic 440 or 420 steel, from biocompatible metals such as tungsten or titanium, or from carbon fiber-reinforced or solid plastic material.

In some embodiments, the system comprises a set of elastic elements with different spring constants to choose from, or an elastic element with an adjustable spring constant. This way, by choosing an elastic element of appropriate spring constant, or by adjusting the spring constant, it can be ensured that for different ranges of forces to be applied or to be generated, the deflection will still be in a certain range for which the detection of the deflection by means of the magnet element and the magnetic field sensor operates with high precision. Also, by choosing an elastic element from a set of elastic elements with different spring constants, various physiological conditions can be mimicked. For example, choosing an elastic element with a comparatively high spring constant for conditioning of cardiovascular tissue could mimic a situation similar to that encountered by cardiac tissue in the real environment when the person suffers from high blood pressure or situations where the person is exercising. Conversely, an elastic element with a lower spring constant could resemble a situation where the patient is at rest. Note in this regard that the expression "spring constant" shall generally reflect a ratio of the applied force and the deflection caused thereby, but shall not imply that this "spring constant" is necessarily a constant in the sense that this ratio is independent of the degree of deflection. Instead, the term "spring constant" shall also cover cases where this ratio is determined by a characteristic force-deflection-curve.

Please note that in prior art setups, forces generated by a cell or tissue culture are typically measured under "isometric conditions", that is without a significant change in length. This may appear attractive for some reasons, since for example a muscle develops the highest contraction force under these conditions, and the force sensors employed only need to allow for minimum movement. However, the contraction of a muscle against a very stiff resistance does not correspond to the natural physiological conditions. In normal tissue, there is a characteristic relationship between force and contraction of cells. This relationship is referred to as the tissue elasticity, which is also referred to as Young's modulus in the art. It has been observed that muscle cells detect this elasticity and adapt their functional features to it. For example, in Chopra A, Tabdanov E, Patel H, Janmey P A, Kresh J Y.: *Cardiac myocyte remodeling mediated by N-cadherin-dependent mechanosensing. Am J Physiol Heart Circ Physiol.* 2011; 300(4):H1252-66, it could be shown that isolated heart muscle cells develop an entirely different cell structure, depending on whether they have been cultivated on a stiff or an elastic surface. According to some embodiments of the present disclosure, the elastic element to be coupled with the cell or tissue culture allows for simulating the elasticity of the surrounding tissue in the natural environment.

In particular, by choosing an elastic element of appropriate spring constant, or by adjusting the spring constant, a desired elasticity of surrounding tissue can be simulated. In many applications, the simulated or mimicked elasticity of surrounding tissue will correspond to the elasticity of healthy tissue, but advantageous uses of the invention are not limited to this. Instead, the system and method of some embodiments of the present disclosure can also be used to simulate pathophysiological conditions which lead to an increased stiffness (for example in case of fibrosis), or a decreased stiffness (for example in case of myopathy). In some uses of the system and method of embodiments of the present disclosure, one may wish to expose the cell or tissue culture to such pathological conditions, for example to study the effects of certain medications or the like. The change of tissue elasticity under pathological conditions in case of myocardium or the muscle layer of a vessel wall have for example been studied in Chaturvedi R R, Herron T, Simmons R, Shore D, Kumar P, Sethia B, Chua F, Vassiliadis E, Kentish J C. *Passive stiffness of myocardium from congenital heart disease and implications for diastole. Circulation.* 2010; 121(8):979-88, and Kim S A, Park S H, Jo S H, Park K H, Kim H S, Han S J, Park W J, Ha J W.: *Alterations of carotid arterial mechanics preceding the wall thickening in patients with hypertension. Atherosclerosis.* 2016; 248:84-90.

In prior art, the usual way of exposing cultivated cells or tissues to specific elasticities involves the use of elastic adhesion substrates. However, at least for heart muscle tissue, this does not correspond to the true physiological conditions in vivo, because muscle cells are predominantly mechanically coupled with each other rather than with the surrounding matrix. The elastic element of the system and apparatus of embodiments of the present disclosure, however, allows for simulating the tissue elasticity by the elastic suspension and thereby also defines the direction of the developed force. If this direction is parallel or nearly parallel to the contracting elements of the muscle cells, this corresponds to the true physiological conditions and is of great advantage for the cultivation and examination of muscle tissue.

In some embodiments, said magnetic element is arranged on said elastic element such that a dipole moment of said magnetic element is arranged at an angle of less than 30°, or in further embodiments less than 20°, or in yet further embodiments less than 12°, with regard to the direction of motion of said magnetic element upon deflection of said elastic element. Simply put, in these embodiments, the magnetic dipole moment of the magnetic element is parallel, or nearly parallel within the above defined limits, with the direction of motion of the magnetic element in operation. As will be demonstrated with reference to a specific embodiment below, this arrangement allows for a particularly precise assessment of the deflection via the measurement of the magnetic field sensor. In an alternative embodiment, said magnetic element is arranged on said elastic element such that a dipole moment of said magnetic element is arranged at an angle that is perpendicular to said direction of motion of said magnetic element, or deviates from this perpendicular direction by less than 30°, or in further embodiments by less than 20°, or in yet further embodiments by less than 12°.

In some embodiments, the system further comprises a culture chamber, wherein in said culture chamber, the elastic element is mounted, or an adapter is provided for mounting said elastic element in said culture chamber in a predetermined position, and outside of said culture chamber, said magnetic field sensor is arranged, or an adapter is provided for mounting said magnetic field sensor in a predetermined position.

Note that in operation of the system, the elastic element is mounted in the culture chamber, and the magnetic field sensor is arranged outside the culture chamber, and the relative positions of the two components have to be adjusted appropriately such as to allow for a precise assessment of the deflection of the elastic element by the corresponding change of magnetic field detected by said magnetic field sensor. One way to achieve this is to have the elastic element be preinstalled in the culture chamber and to have the magnetic field sensor be prearranged outside the culture chamber, but the present disclosure is not limited to this. Instead, it is also possible to provide corresponding adapters for mounting or arranging the elastic element and/or the magnetic field sensor at the predetermined positions. In some embodiments, the elastic element would be preinstalled in the culture chamber, while the magnetic field sensor is only mounted by the user using the aforementioned adapter. In this scenario, the culture chamber and the elastic element could be part of a disposable product, because these are the cheap components and the components that become contaminated during use, while the magnetic fields sensor, that will not be exposed to the environment within the culture chamber, can be easily reused.

As referred to herein, the term "adapter" shall have a broad meaning and shall cover any device or means assisting the user in attaching the respective component precisely at a predetermined position, and could for example be resembled by a receptacle for receiving the magnetic field sensor, pre-fabricated bores or internal threads for receiving screws for attaching the magnetic field sensor in place or the like.

When said elastic element and said magnetic field sensor are mounted inside and outside said culture chamber, respectively, and said elastic element is in an un-deflected state, in some embodiments said magnetic field sensor and said magnetic element are separated by 1 cm or less, in further embodiments by 5 mm or less, in yet further embodiments by 4 mm or less and in even further embodiments by 3 mm or less, and/or in some embodiments by 0.5 mm or more, in further embodiments by 0.9 mm or more, in yet further embodiments by 1.3 mm or more, and in even further embodiments by 1.5 mm or more. This way, sufficient space is provided for accommodating a separator wall of the culture chamber between the magnetic field sensor and the magnetic element, while at the same time the distance is sufficiently small that a precise assessment of the motion of the magnetic element, and hence the deflection state of the elastic element, can be achieved.

In some embodiments, the system further comprises a first holding element, said first holding element comprising a holding section for holding said cell or tissue culture, and a coupling section for coupling with said elastic element.

In some embodiments, the system further comprises a drive mechanism for applying a force, in particular a tensile force to said cell or tissue culture. Herein, the system may further comprise a second holding element, said second holding element comprising a holding section for holding said cell or tissue culture and a coupling section for coupling with said drive mechanism.

In some embodiments, said holding section of said first and/or second holding elements comprises a clamping device for clamping said cell or tissue culture, a holder that is attached with or attachable with adhesive to native or artificially generated tissues, or a fixation to be integrally cast with a cell/matrix mixture.

In some embodiments, the system further comprises a control unit, said control unit being connected to receive signals representing magnetic field information obtained with said magnetic field sensor, and connected with said drive mechanism to control the force applied to said cell or tissue culture at least in part in response to said signal representing magnetic field information.

Herein, the "signals representing magnetic field information" could e.g. be the raw data obtained with the magnetic field sensor, based on which the control unit could calculate the degree of deflection of the elastic element or even the force associated therewith, based on an underlying spring constant or characteristic spring constant curve. However, the "signals representing magnetic field information" could also be information already derived from the processed raw data, such as the degree of deflection, or the force, or any intermediate parameter, as long as it is derived from the magnetic field information.

In response to the signal representing magnetic field information, the control unit can then control the force applied to said cell or tissue culture, such as to achieve a desired mechanical stimulation thereof. In some embodiments, the system further comprises one or more electrodes for applying electrical stimuli to said cell or tissue culture, wherein said stimuli are likewise controlled by said control unit. This way, the mechanical and electrical stimulation can be coordinated under the control of the same control unit.

A further aspect of the present disclosure relates to a method for determining a force applied to or generated by a cell or tissue culture arranged in a culture chamber comprising the following steps: providing said culture chamber, coupling an elastic element mounted in said culture chamber with said cell or tissue culture such that a force applied to or generated by said cell or tissue culture leads to a deflection of said elastic element against a restoring force thereof, said elastic element forming or comprising a magnetic element arranged such as to be moved upon deflection of said elastic element, and detecting a change of magnetic field attributable to a corresponding movement of said magnetic element upon deflection of said elastic element using a magnetic field sensor that is separated from said elastic element by a separating wall.

In some embodiments, the method uses a system as specified above and/or described in the following detailed description and/or claimed in the attached claims. Some embodiments of the method may further comprise on or more of the following steps or operations: (i) measuring a magnetic field component in a direction perpendicular and/or parallel to the direction of motion direction of said magnetic element upon said deflection of said elastic element; (ii) measuring at least two, preferably at least three linearly independent magnetic field components using said magnetic field sensor; and (iii) translating a measurement result of said magnetic field sensor into a parameter representing the deflection of said elastic element and/or a force applied to or generated by said cell or tissue culture.

In some embodiments, the method comprises a step of selectively choosing an elastic element of appropriate spring constant, or adjusting the spring constant of an elastic element, such that an assumed elasticity of surrounding tissue, which the cell or tissue culture would experience in vivo, is simulated.

In some embodiments, the assumed elasticity of surrounding tissue corresponds to the elasticity of healthy tissue. In further embodiments, the assumed elasticity of surrounding tissue corresponds to pathologic physiological conditions. In various embodiments, the pathophysiological conditions correspond to conditions with increased stiffness as compared to healthy tissue, and in particular to the presence of fibrosis. In other embodiments, the pathological physiological conditions correspond to conditions with decreased stiffness as compared to healthy tissue, and in particular to the presence of myopathy. In some further embodiments, the method comprises the steps of exposing the cell or tissue culture to an assumed elasticity corresponding to such pathological conditions and a step of studying the effects of certain medications on the cell or tissue culture under these conditions.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure, and are therefore, not to be considered limiting of its scope. The disclosure will be described with additional specificity and detail through use of the accompanying drawings.

In the drawings.

DESCRIPTION OF EMBODIMENTS OF THE DISCLOSURE

Figure 1:
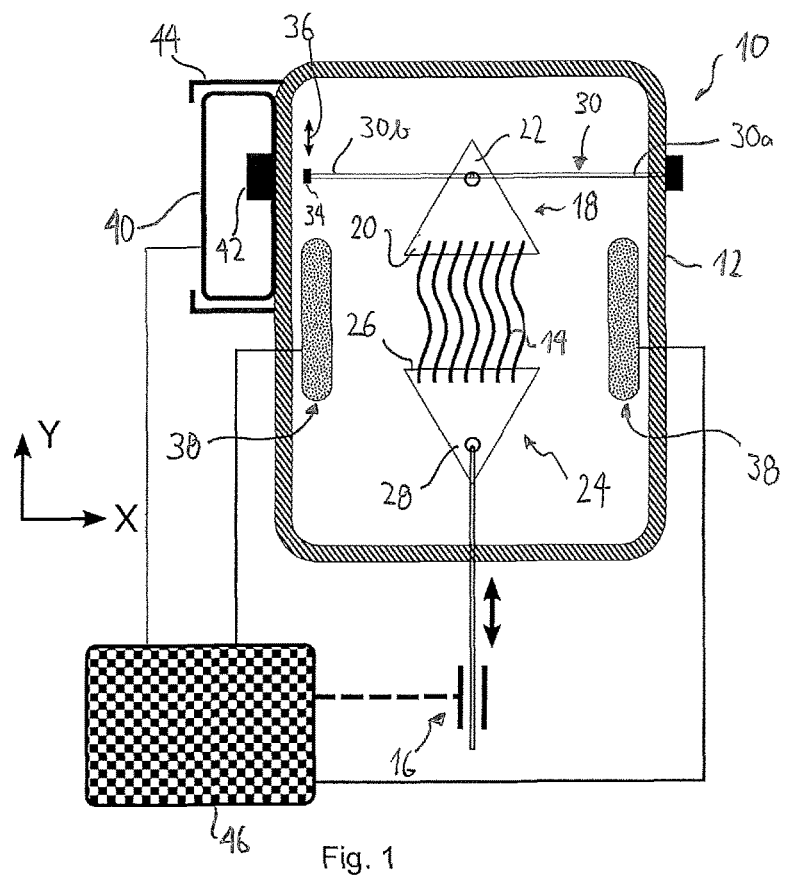
FIG. 1 illustrates a schematic view of a system according to an embodiment of the invention.

For the purposes of promoting an understanding of the principles of the disclosure, reference will now be made to an embodiment illustrated in the drawings, and specific language will be used to describe the same. It will nevertheless be understood that no limitation of the scope of the invention is thereby intended, such alterations and further modifications in the illustrated apparatus and such further applications of the principles of the disclosure as illustrated therein being contemplated as would normally occur now or in the future to one skilled in the art to which the invention relates.

FIG. 1 illustrates a schematic representation of a system 10 according to an embodiment of the present invention. As seen therein, the system 10 comprises a culture chamber 12 in which a cell or tissue culture schematically shown at 14 is arranged. The cell or tissue culture 14 could for example be a piece of functional bioartificial cardiac tissue that could serve as an artificial patch for transplantation. While not shown in FIG. 1, the culture chamber 12 further includes a nutrition solution which is kept at physiologic temperatures, such that warm and humid conditions are present inside the culture chamber 12.

As is explained for example in Kensah, G. et al., an optimal tissue replacement should be able to exert contractile forces comparable to that of native cardiac tissue. By mechanically stretching the cell or tissue culture, the tissue formation and contractility of the bioartificial cardiac graft can be improved. For this purpose, a linear drive 16 is provided for applying a force, more precisely a tensile force to the cell or tissue culture 14. More precisely, the cell or tissue culture 14 is held by a first and a second holding element 18, 24, respectively. Herein, the second holding element 24 has a holding section 26 for holding said cell or tissue culture 14, and a coupling section 28 for coupling with the linear drive 16. The first holding element 18 likewise has a holding section 24 for holding the opposite end of the cell or tissue culture 14, and a coupling section 22 for coupling with a rod 30, which rod 30 resembles an example of the "elastic element" referred to in the introductory portion of the description.

While not shown in detail in FIG. 1, the holding sections 20 and 26 of said first and second holding element 18, 24 could each be a rod that is integrally cast with a cell/matrix mixture in a similar way as disclosed in Kensah, G. et al. Alternatively, the holding sections 20 and 26 of said first and second holding elements 18, 24 could include a clamping device for clamping the cell or tissue culture 14. Instead of using a clamping device, native or bioartificial tissue, or matrix prepared for cell seeding can be attached to the holding elements 18, 24 by cyanoacrylate or protein-based adhesives, as described by Brandenburger, M. et al., *Cardiovasc Res.* 2012; 93(1): 50-9.

With further reference to FIG. 1, the rod 30 is made from surgical grade steel. In some embodiments, the rod 30 may additionally be coated with a biocompatible material, such as Teflon or Parylene. The rod 30 has a fixed end 30a that is attached to a wall of the culture chamber 12 using a fastener 32. Opposite to the fixed end 30a, the rod 30 has a free end 30b at which a magnetic element 34 is disposed. In the embodiment shown, the magnetic element 34 is a permanent magnet that is coated with a biocompatible material. More precisely, the magnetic element 34 is a permanent magnet made from an AlNiCo alloy that is goldplated and that is further coated with Parylene or Teflon. When a tensile force is applied to the cell or tissue culture 14 by means of the linear drive 16, this force leads to a deflection of the rod 30, and consequently to a movement of the magnetic element 34, wherein the direction of the movement of the magnetic element 34 is indicated by the arrow 36 in FIG. 1. Moreover, the magnetic element 34 is arranged such that its magnetic dipole moment is parallel to this direction of motion, or at most tilted with regard to this direction of motion by 30°, and in further embodiments by less than 20°, and in yet further embodiments by less than 12°.

Finally, stimulating electrodes 38 are provided inside the culture chamber 12, which are devised for applying electrical stimuli to the cell or tissue culture 14. Each of the cell or tissue culture 14, the first and second holding elements 18, 24, the rod 30 and the stimulating electrodes 38 are arranged inside the culture chamber 12, and are hence exposed to the humid atmosphere kept at physiological conditions therein.

Outside the culture chamber 12, a sensor module 40 is provided, which includes a magnetic field sensor 42. The sensor module 40 is removably attached to the culture chamber 12 by means of a receptacle 44 schematically shown in FIG. 1. The receptacle 44 is an example of the "adapter" referred to in the introductory portion of the specification. The magnetic field sensor 42 is capable of measuring the magnetic field strength, more precisely the magnetic flux density in three dimensions X, Y and Z, wherein the dimensions X and Y are indicated by the coordinate system shown in FIG. 1, and wherein the dimension Z is perpendicular to the paper plane.

Finally, the system 10 comprises a control unit 46, which is operatively connected with the linear drive 16 and the stimulation electrodes 38 for controlling the same, and which is connected to receive signals representing magnetic field information obtained with said magnetic field sensor 42 from the sensor module 40.

Next, the function of the system 10 shown in FIG. 1 is explained with reference to FIGS. 2 to 5.

Figure 2:
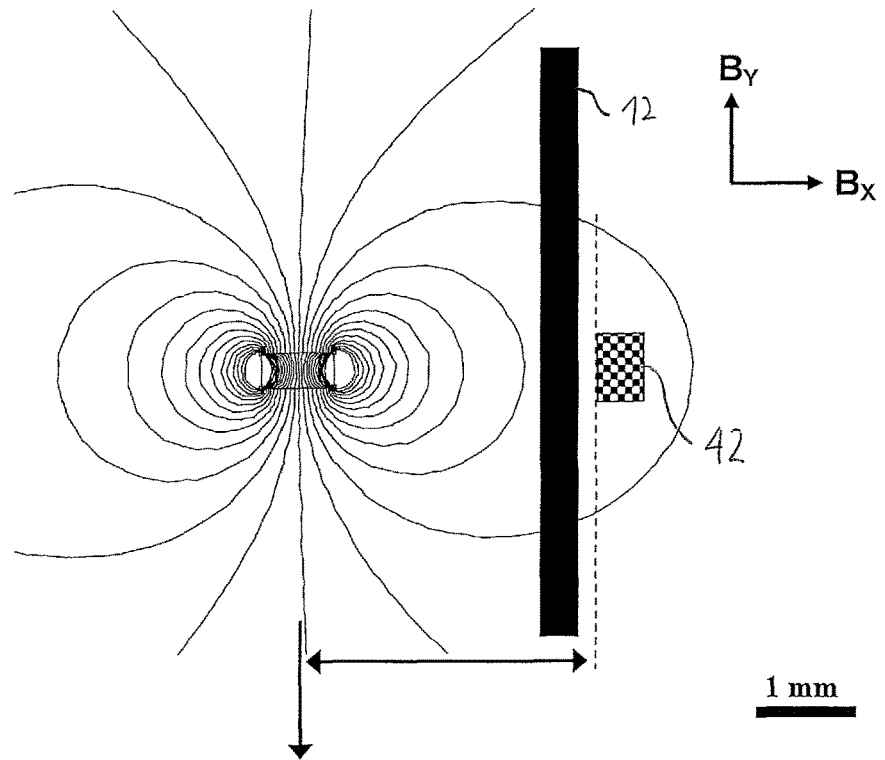
FIG. 2 illustrates a close up view of the magnetic element and the magnetic field sensor of the system of FIG. 1, further showing the magnetic field generated by the magnetic element.
Figure 3:
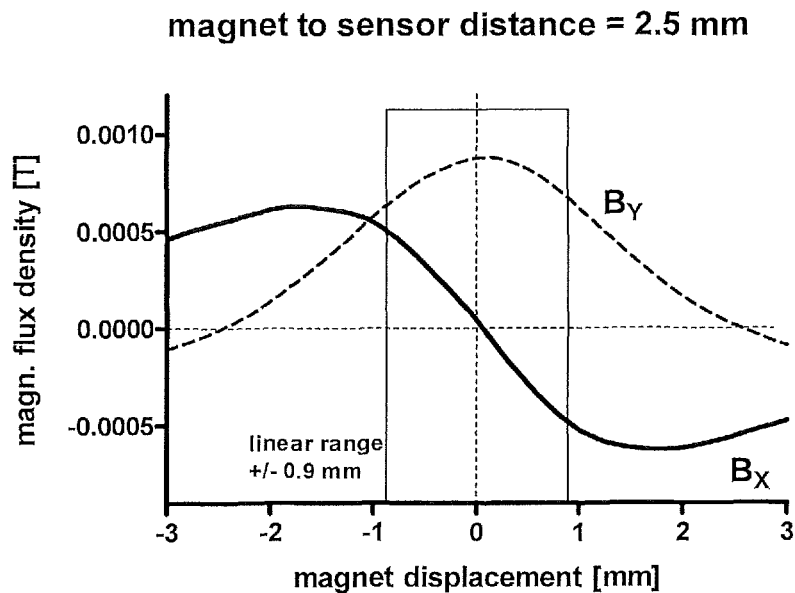
FIG. 3 illustrates the magnetic flux density in two directions measured by the magnetic field sensor, as a function of the deflection of the elastic rod of the system of FIG. 1.

FIG. 2 illustrates a close up view of the magnetic field sensor 42, the magnetic element 34, the wall of the culture chamber 12 separating the magnetic field sensor 42 from the magnetic element 34 as well as the magnetic field generated by the magnetic element 34. When the magnetic element 34 is moved downwards in FIG. 2, upon deflection of the rod 30 in response to a tensile force applied by said linear drive 16, the magnetic flux density both for the X and the Y component measured by the magnetic field sensor 42 will change, as demonstrated in FIGS. 3 and 4. FIG. 3 shows the magnetic flux densities $B_X$ and $B_Y$ measured by the magnetic field sensor 42 in X and Y direction as a function of deflection of the free end 30b of the rod 30, or in other words, as a function of the movement of the magnetic element 34, provided that the magnetic element 34 and the magnetic field sensor 42 are arranged at a distance of 2.5 mm apart.

Figure 4:
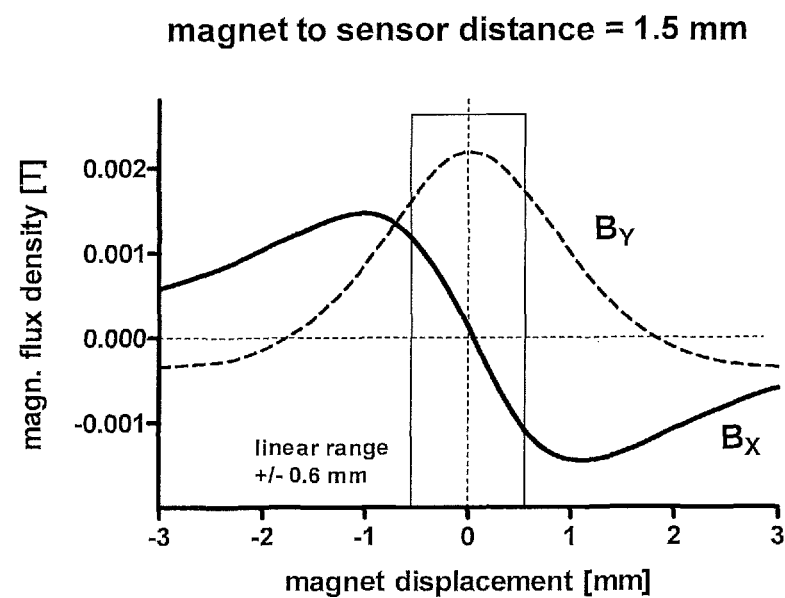
FIG. 4 illustrates similar flux densities as FIG. 3, but with a smaller distance between the magnetic field sensor and the magnetic element.

FIG. 4 illustrates the same parameters in a situation where the magnetic element 34 and the magnetic field sensor 42 are arranged at a distance of only 1.5 mm. Both of these distances are sufficient to accommodate a wall of a culture chamber 12 in between, or in other words, to arrange the magnetic element 34 inside and the magnetic field sensor 42 outside the culture chamber 12.

As can be discerned from FIG. 3, at a distance of 2.5 mm, the magnetic flux density in X direction is an approximately linear function of the dislocation of the magnetic element 34 within a range of −0.9 mm to +0.9 mm with respect to a rest position. It was found that from the measured flux density in X direction alone, the dislocation of the magnetic element 34 due to deflection of the rod 30 could be measured with a resolution of 3 µm.

When the distance between the magnetic element 34 and the magnetic field sensor 42 is decreased to 1.5 mm, the relative resolution of the magnetic flux density becomes expectedly higher, but the linear region becomes more narrow, as indicated by the shaded area in FIG. 4, and in fact decreases to a range from −0.6 mm to +0.6 mm.

Figure 5:
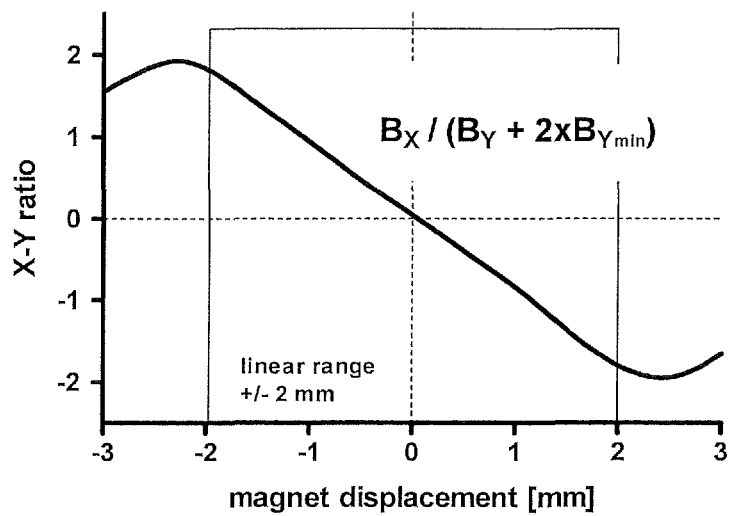
FIG. 5 illustrates a combined parameter derived from the flux densities of FIG. 4, as a function of the deflection of the elastic rod of the system of FIG. 1.

FIG. 5 illustrates an example, where a combined parameter is calculated from $B_X$ and $B_Y$ according to the formula $B_X/(B_Y+2\times B_{Ymin})$, where $B_{Ymin}$ corresponds to the minimum value of $B_Y$ in FIG. 5. As seen from FIG. 5, this combined parameter, even when measured at a distance of only 1.5 mm between the magnetic element 34 and the magnetic field sensor 42, shows a linear behavior in a much larger range of dislocations from about −2.0 mm to +2.0 mm.

In the embodiment shown, the magnetic field components $B_X$ and $B_Y$ are digitized within the sensor module 40 and transferred to the control unit 46, where the combined parameter of FIG. 5 is calculated therefrom. Accordingly, in this embodiment the control unit 46 resembles an example of the aforementioned logic element suitable for translating the measurement result of the magnetic field sensor 42 into a parameter representing the deflection of the "elastic element". The control unit 46 can then, based on a known force-deflection-curve of the rod 30 likewise calculate the force applied to the cell or tissue culture 14.

Based on the thus determined force applied to the cell or tissue culture 14, the control unit 46 can then provide for a desired mechanical stimulation, which can be accompanied by a suitable electrical stimulation using the stimulating electrodes 38.

As is seen from FIGS. 3 to 5, the detection of the deflection by means of the magnetic field sensor 42 works well within a certain range of deflections. In order to provide for a wide range of forces that can be measured, in one embodiment of the invention, a set of elastic rods 30 can be provided with different spring constants to choose from, so that depending on the desired force to be applied to the cell or tissue culture 14, a rod 30 can be chosen that will largely exhaust, but not exceed the range of deflection corresponding to the shaded area in FIG. 5.

Figure 6:
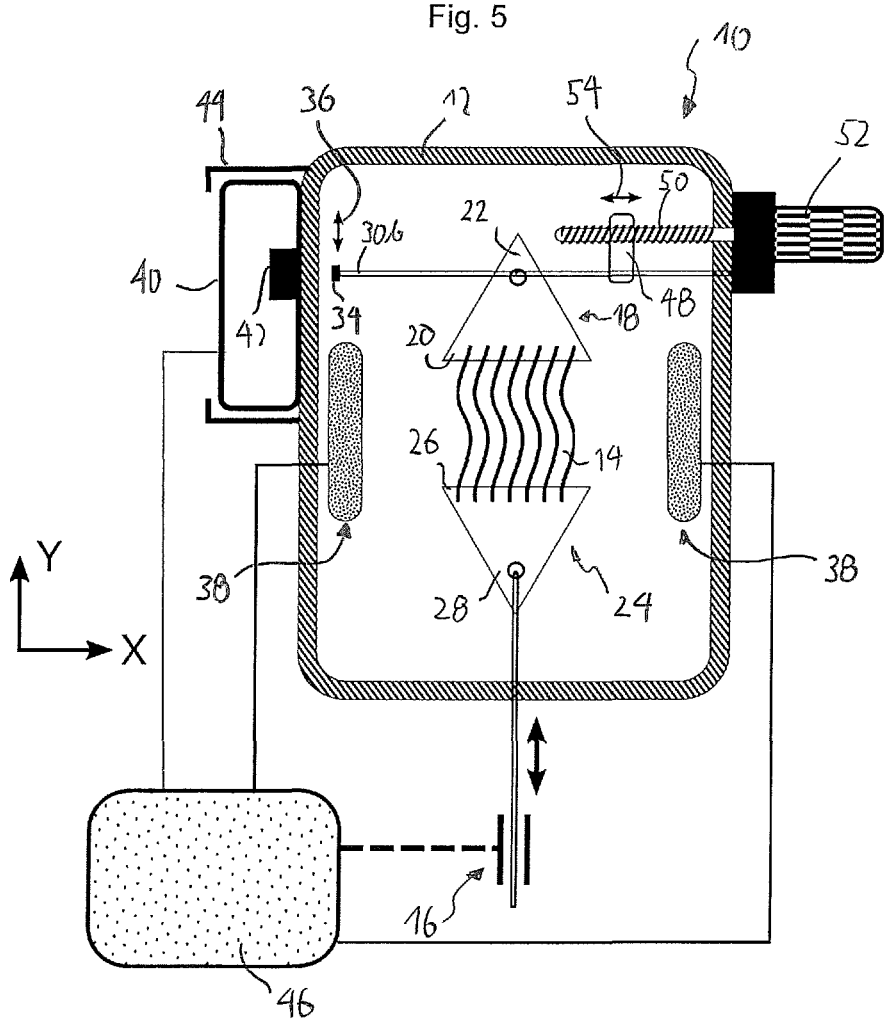
FIG. 6 illustrates an elastic element with an adjustable spring constant.

Instead of providing a set of rods with different spring constants, it is also possible to provide a rod 30 with an adjustable spring constant. For example, the rod 30 may be provided with a rigid sleeve 48 that can be slipped on the rod 30 to locally stiffen the same and hence increase the spring constant of the rod 30, as shown in FIG. 6. The spring constant can be further adjusted by the position of the sleeve 48 on the rod 30 by means of a threaded connection between a threaded element 50 and the sleeve 48. By turning a knob 52 connected with said threaded element 50, the position of the sleeve 48 can be adjusted along a direction indicated by arrows 54.

In the embodiment shown, the culture chamber 12 with the rod 30 pre-mounted therein is a disposable product, that is not to be reused. However, using the fastener 32, it is easy for the manufacturer to pre-assemble the culture chamber 12 with rods 30 of different strengths and correspondingly different spring constants. The sensor module 40, on the other hand, is reused and can be easily combined with any fresh culture chamber 12, by simply inserting the same into the receptacle 44 shown in FIG. 1. Importantly, the receptacle 44 is arranged such that when the sensor module 40 is received therein, the magnetic field sensor 42 included in the sensor module 40 will be appropriately arranged with regard to the magnetic element 34 provided at the free end 30b of the rod 30.

As mentioned in the introductory portion of the specification, in some embodiments the elastic element 30 itself may be magnetic, such that no additional magnetic element needs to be provided. Instead, in such an embodiment, the elastic element itself forms the "magnetic element" referred to herein.

Figure 7:
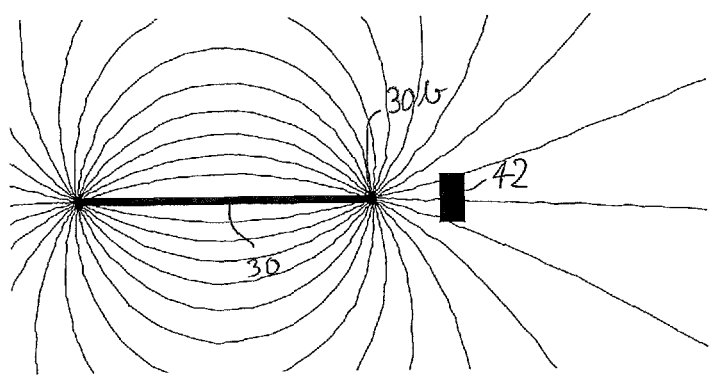
FIG. 7 illustrates the magnetic field distribution in an embodiment in which the elastic element itself is magnetic.
Figure 8:
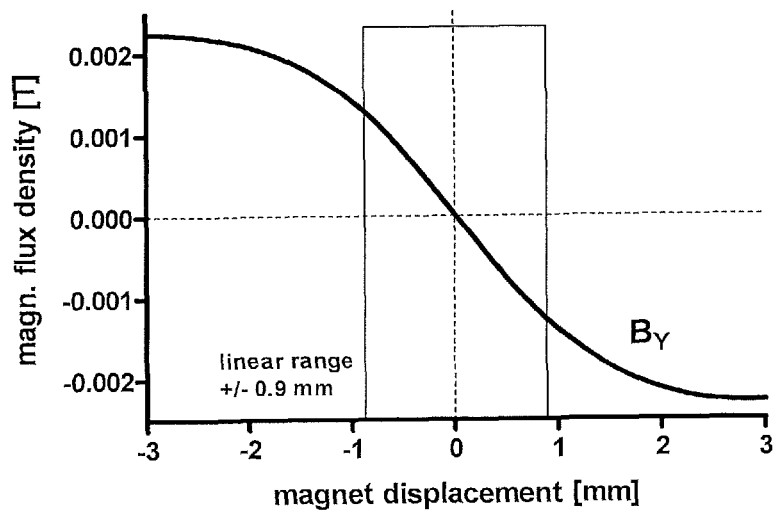
FIG. 8 illustrates the magnetic field component parallel to the direction of motion of the tip of the elastic element of FIG. 7 upon deflection.

FIG. 7 illustrates the magnetic field distribution of a magnetic elastic rod 30 and a magnetic field sensor 42 arranged in said magnetic field. FIG. 8 shows the magnetic field component parallel to the direction of motion of the tip 30b of the elastic element 30 upon deflection of the elastic element as measured by the magnetic field sensor 42. From the geometry of the magnetic field shown in FIG. 7, it will be appreciated that without deflection, i.e. for vanishing magnet displacement, the magnetic field strength is zero. As further shown in FIG. 8, if the tip 30b of the magnetic elastic element 30 is displaced within a range of ±0.9 mm, the magnetic field strength varies approximately proportionally with the displacement of the tip 30b (referred to as "magnet displacement" in FIG. 8).

Figure 9:
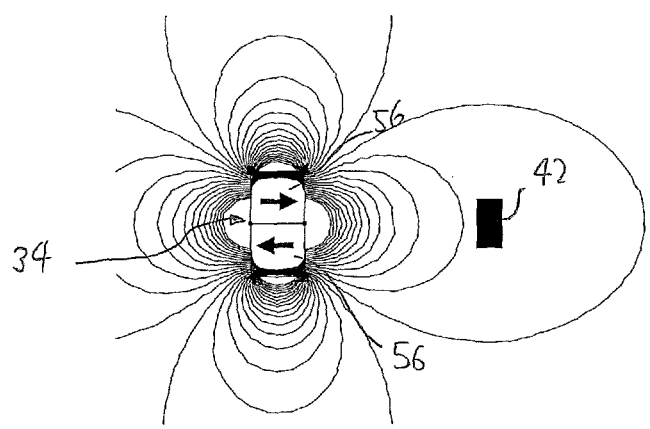
FIG. 9 illustrates the magnetic field distribution for an embodiment in which the magnetic element is formed by two anti-parallel permanent magnets.

FIG. 9 illustrates the magnetic field distribution for a further embodiment, in which the magnetic element 34 is formed by two anti-parallel permanent magnets 56, and the magnetic field sensor 42 is arranged in the corresponding magnetic field.

Figure 10:
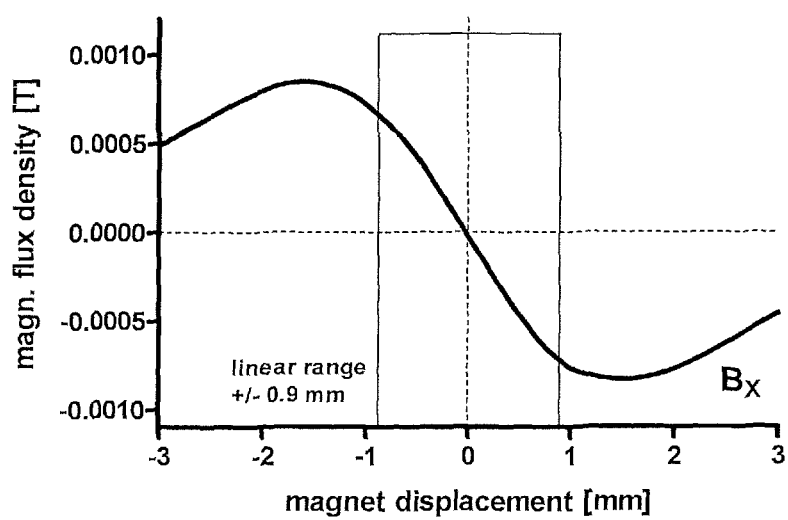
FIG. 10 illustrates the magnetic field component perpendicular to the direction of motion of the tip of the elastic element.

FIG. 10 illustrates the magnetic field component perpendicular to the direction of motion of the magnetic element 34 as measured by the magnetic field sensor 42 upon deflection of the corresponding elastic element 30 (not shown). In FIG. 9, this direction of motion corresponds to a vertical movement. From the geometry of the magnetic field shown in FIG. 9, it will be appreciated that in the rest position shown in the figure (i.e. without deflection), the magnetic field strength perpendicular to the direction of motion is zero. As is further seen from FIG. 10, in the vicinity of the rest position shown in FIG. 9, the magnetic field strength varies approximately proportionately with the displacement of the magnetic element 34 in the vertical direction.

The ability of the described tissue culture system 10 to maintain vitality and functionality of myocardium in vitro was tested with a typical application. Samples of adult human myocardium 14 were obtained from explanted failing hearts of consenting patients receiving a heart transplant.

Figure 11:
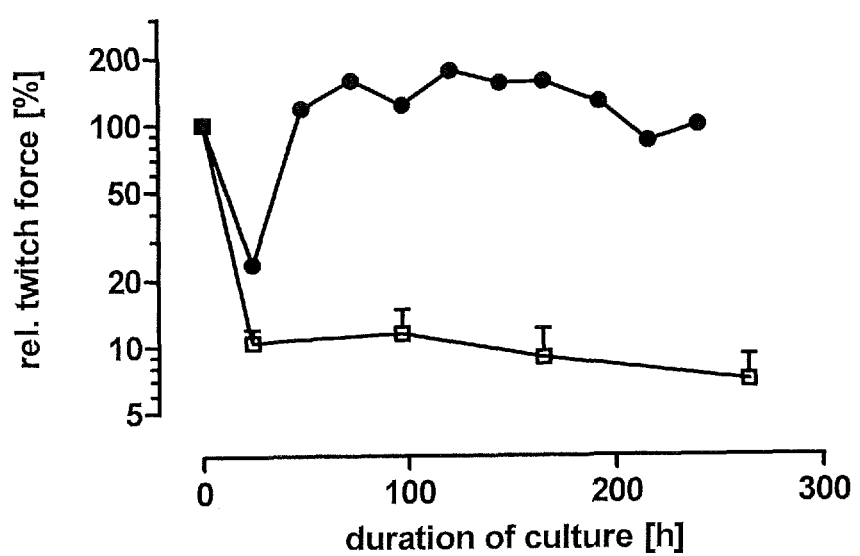
FIG. 11 illustrates a diagram showing the relative twitch force versus cultivation time for samples of adult human myocardium cultivated in a system according to FIG. 1.

The tissue was cut into thin slices according to an established procedure as described in Brandenburger M, Wenzel J, Bogdan R, Richardt D, Nguemo F, Reppel M, Hescheler J, Terlau H, Dendorfer A. *Organotypic slice culture from human adult ventricular myocardium. Cardiovasc Res*, 93(1), 50-59, 2012. Vital tissue specimen were glued to triangle tissue holders 18, 24, and were mounted in culture chambers 12, as exemplified in FIG. 1. By means of the described technique, a passive strain could be applied that resembled physiological diastolic stress of the cardiac wall. Under continuous electrical stimulation (0.2 Hz, 1 ms pulse duration, bipolar), active contractions were recorded over a culture period of up to 10 days. In comparison to the force development of hypertrophic human myocardium subjected to a previously established technique of tissue cultivation in a quiescent state (square symbols in FIG. 11), contractile performance was better preserved under biomimetic conditions (round symbols in FIG. 11). It is hence seen that the system 10 of FIG. 1 allows for: well controlled biomechanic conditions and relevant readouts, long-term functional preservation, thus enabling chronic manipulation and the investigation of protracted alterations, and continuous measurement of contractility, thus e.g. enabling assessment of drug effects in a single tissue specimen.

In general, it is expected that the culture technique described for adult myocardial tissues will also improve the maturation of artificial tissues engineered from differentiated stem cells and a biocompatible matrix. Furthermore, its application to any kind of mechanosensitive tissue (e.g. skeletal muscle, smooth muscle from vessel, gut, bronchi, etc., connective tissue, tendon, cartilage, bone etc.) can be envisaged.

As was explained above, an important advantage of the system and method of the invention is that the spring constant of the elastic element 30 allows for simulating in vitro the elasticity of the surrounding tissues with the cell or tissue culture would experience in its natural physiological environment, i.e. in vivo.

To give a specific example, it shall be assumed that for the culture of a heart muscle, the Young's modulus of the heart muscle in systole shall be simulated. As can be taken from Hassaballah A1, Hassan M A, Mardi A N, Hamdi M. *An inverse finite element method for determining the tissue compressibility of human left ventricular wall during the cardiac cycle. PLoS One.* 2013; 8(12):e82703, this Young's modulus may amount to about 500 kPa. It follows that for a sample size of 5×5×0.3 mm$^3$ (length×width×thickness), and for a contraction of 0.5 mm, a force of 500 mN/mm$^2$×5 mm×0.3 mm×0.5 mm/5 mm=75 mN is generated. In order to simulate the elasticity of the surrounding tissue, an elastic element 30 with a spring constant of 150 mN/mm is therefore needed. This can be for example achieved in the setup shown above with a rod 30 formed by steel wire having an effective length of 10 mm and a diameter of 0.28 mm. Namely, the spring constant of a bending rod is defined as $3 \times E \times Iy/l^3$ with E (elastic modulus)=180 GPa for V2A steel and Iy (second moment of inertia)=$r^4 \times \pi$ for a cylindrical rod. With these values, a spring constant $3 \times E \times r^4 \times \pi/4/l^3$ of 150 mN/mm is obtained.

Although exemplary embodiments are shown and specified in detail in the drawings and the preceding specification, these should be viewed as purely exemplary and not as limiting the invention. It is noted in this regard that only exemplary embodiments are shown and specified, and all variations and modifications should be protected that presently or in the future lie within the scope of protection of the invention as defined in the claims, including any equivalents.

REFERENCE SIGN LIST 10 system
12 culture chamber
14 cell or tissue culture
16 linear drive
18 first holding element
20 holding section
22 coupling section
24 second holding element
26 holding section
28 coupling section
30 rod
30a fixed end
30b free end
32 fastener
34 magnetic element
36 arrows
38 stimulating electrodes
40 sensor module
42 magnetic field sensor
44 receptacle
46 control unit
48 sleeve
50 threaded element 52 knob
54 arrows
56 permanent magnet

The invention claimed is:

1. A system for determining a force applied to or generated by a cell or tissue culture arranged in a culture chamber, the system comprising:
a culture chamber;
an elastic element arranged in said culture chamber, said elastic element being adapted to be coupled with said cell or tissue culture such that a force applied to or generated by said cell or tissue culture leads to a deflection of said elastic element against a restoring force thereof, and said elastic element forming or comprising a magnetic element arranged such as to be moved upon deflection of said elastic element; and
a magnetic field sensor, which is mounted outside of said culture chamber and is separated from said elastic element by a separating wall of said culture chamber, said magnetic field sensor being adapted to detect a change of magnetic field attributable to a corresponding movement of said magnetic element upon deflection of said elastic element, wherein said elastic element comprises a rod or beam, said deflection amounts to a bending of said rod or beam, said rod or beam has a fixed end mounted to said culture chamber and a free end opposite to said fixed end, and said magnetic field sensor is arranged in proximity to said free end of said rod or beam and distally to said fixed end of said rod or beam.

2. The system of claim 1, wherein said magnetic field sensor is suitable for measuring a magnetic field component in a direction that is at least one of (i) perpendicular to the direction of motion of said magnetic element upon said deflection of said elastic element, or (ii) parallel to the direction of motion of said magnetic element upon said deflection of said elastic element.

3. The system of claim 1, wherein said magnetic field sensor comprises a magnetic sensor suitable for measuring at least two linearly independent magnetic field components.

4. The system of claim 1, further comprising a logic element suitable for translating a measurement result of said magnetic field sensor into a parameter representing at least one of (i) the deflection of said elastic element, or (ii) a force applied to or generated by said cell or tissue culture.

5. The system of claim 4, wherein said measurement result to be translated by a said logic element represents at least two linearly independent magnetic field components.

6. The system of claim 4, wherein said logic element comprises one or both of an integrated circuit and a microprocessor.

7. The system of claim 1, wherein said rod or beam is made from stainless steel.

8. The system of claim 7, wherein said stainless steel comprises surgical stainless steel, the surgical stainless steel including at least on or more of austenitic 316 stainless steel, or martensitic 440 or 420 steel.

9. The system of claim 1, wherein the system comprises an elastic element with an adjustable spring constant.

10. The system of claim 1, wherein said magnetic element is arranged on said elastic element such that a dipole moment of said magnetic element is arranged at an angle of less than 30° with regard to the direction of motion of said magnetic element, or is perpendicular to said direction of motion of said magnetic element, or deviates from this perpendicular direction by less than 30°.

11. The system of claim 1, wherein, when said elastic element is in an undeflected state, said magnetic field sensor and said magnetic element are separated by at most 1 cm.

12. The system of claim 1, wherein the culture chamber and the elastic element are disposable products.

13. The system of claim 1, further comprising a first holding element, said first holding element comprising a holding section for holding said cell or tissue culture and a coupling section for coupling with said elastic element.

14. The system of claim 13, further comprising a drive mechanism for applying a tensile force to said cell or tissue culture.

15. The system of claim 14, further comprising a second holding element, said second holding element comprising a holding section for holding said cell or tissue culture and a coupling section for coupling with said drive mechanism.

16. The system of claim 13, wherein said holding section of said first holding element comprises a clamping device for clamping said cell or tissue culture, a holder that is attached with or suitable for attaching with adhesive to native or artificially generated tissues or a fixation to be integrally cast with a cell/matrix mixture.

17. The system of claim 1, further comprising a control unit, said control unit being connected to receive signals representing magnetic field information obtained with said magnetic field sensor and connected to a drive mechanism to control the force applied to said cell or tissue culture based, at least in part, responsive to said signal representing magnetic field information.

18. The system of claim 17, wherein said system further comprises one or more electrodes for applying electrical stimuli to said cell or tissue culture, wherein said stimuli are controlled by said control unit.

19. The system of claim 1, wherein said rod or beam is made from biocompatible metals comprising tungsten or titanium.

20. The system of claim 1, wherein said rod or beam is made from carbon fiber reinforced plastic material or solid plastic material.

21. The system of claim 1, wherein said rod or beam comprises a coupling point which is adapted to be coupled to said cell or tissue culture via a first holding element such that any force between said first holding element and said rod or beam acts at the coupling point.

22. The system of claim 1, further comprising a sleeve on said rod or beam, and a mechanism which allows a position of the sleeve on said rod or beam to be adjusted along a longitudinal extension of said rod or beam.

23. The system of claim 1, wherein said rod or beam is mounted to said culture chamber at a mounting wall that is an integral part of said culture chamber.

24. A method for determining a force applied to or generated by a cell or tissue culture arranged in a culture chamber, the method comprising:
providing said culture chamber;
coupling an elastic element arranged in said culture chamber with said cell or tissue culture such that a force applied to or generated by said cell or tissue culture leads to a deflection of said elastic element against a restoring force thereof, said elastic element forming or comprising a magnetic element arranged such as to be moved upon deflection of said elastic element; and
detecting a change of magnetic field attributable to a corresponding movement of said magnetic element upon deflection of said elastic element using a magnetic field sensor that is mounted outside of said culture chamber and is separated from said elastic element by a separating wall of said culture chamber, wherein said elastic element comprises a rod or beam, said deflection amounts to a bending of said rod or beam, said rod or beam has a fixed end mounted to said culture chamber and a free end opposite to said fixed end, and said magnetic field sensor is arranged in proximity to said free end of said rod or beam and distally to said fixed end of said rod or beam.

* * * * *